(12) United States Patent
Fung et al.

(10) Patent No.: US 8,004,152 B2
(45) Date of Patent: Aug. 23, 2011

(54) ELECTRONIC TONGUE SENSOR

(75) Inventors: Ying Sing Fung, Ap Lei Chau (HK); Hui Sun, Hong Kong (HK); Zhihong Mo, Hong Kong (HK); Derong Zhu, Hong Kong (HK); Tsz Shan Jacqueline Choy, Ma On Shan (HK); Yin Yee Lee, Ap Lei Chau (HK)

(73) Assignee: The University of Hong Kong, Hong Kong (HK)

( * ) Notice: Subject to any disclaimer, the term of this patent is extended or adjusted under 35 U.S.C. 154(b) by 85 days.

(21) Appl. No.: 12/208,262

(22) Filed: Sep. 10, 2008

(65) Prior Publication Data

US 2009/0212663 A1 Aug. 27, 2009

Related U.S. Application Data

(60) Provisional application No. 60/971,258, filed on Sep. 10, 2007.

(51) Int. Cl.
*G01P 15/09* (2006.01)
(52) U.S. Cl. .................. 310/323.21; 310/311; 427/100; 73/514.34
(58) Field of Classification Search .................. 427/100; 310/323.21, 311; 73/514.34
See application file for complete search history.

(56) References Cited

U.S. PATENT DOCUMENTS

| | | | |
|---|---|---|---|
| 5,719,324 A * | 2/1998 | Thundat et al. ............. 73/24.01 | |
| 6,730,201 B1 | 5/2004 | Kuhlman et al. | |
| 6,841,053 B2 | 1/2005 | Winquist et al. | |
| 6,996,478 B2 * | 2/2006 | Sunshine et al. ................ 702/22 |
| 7,159,463 B2 * | 1/2007 | Dayagi et al. ................... 73/579 |
| 7,316,899 B2 | 1/2008 | McDevitt et al. | |
| 2002/0010495 A1 * | 1/2002 | Freed et al. ...................... 607/42 |
| 2003/0100436 A1 * | 5/2003 | Takahashi ...................... 501/134 |
| 2004/0042931 A1 | 3/2004 | Wit et al. | |
| 2004/0080319 A1 * | 4/2004 | Merrill .......................... 324/439 |
| 2004/0126814 A1 * | 7/2004 | Singh et al. ..................... 435/7.1 |
| 2004/0191918 A1 | 9/2004 | Isz et al. | |
| 2005/0013738 A1 * | 1/2005 | Schwalbe et al. .............. 422/67 |
| 2006/0257883 A1 * | 11/2006 | Bjoraker et al. .................. 435/6 |
| 2008/0144002 A1 | 6/2008 | Murray et al. | |

FOREIGN PATENT DOCUMENTS

WO 02/103340 12/2002

OTHER PUBLICATIONS

Ciosek P, Wróblewski W., "Sensor Arrays for Liquid Sensing—Electronic Tongue Systems", *Analyst*, Oct. 2007;132(10):963-78. Epub Jul. 30, 2007.
Codinachs et al., "Electronic Integrated Multisensor Tongue Applied to Grape Juice and Wine Analysis", Analyst, 2008, DOI: 10.1039/b801228h.
Sherrit et al., "BAW and SAW Sensors for In-situ Analysis", Paper 5050-11, Proceedings of the SPIE Smart Structures Conference, San Diego, CA, Mar. 2-6, 2003.
Winquist et al. , "Theme Article—Electronic Tongues", vol. 29, No. 10, Oct. 2004.

(Continued)

*Primary Examiner* — Thomas M Dougherty
*Assistant Examiner* — Bryan P Gordon

(57) ABSTRACT

The disclosure may relate to example embodiments of an electronic tongue sensor that may include an array of piezoelectric quartz crystal sensors with at least one coating specific for sensing a specific taste-producing molecule. In an example embodiment, a coating may include molecularly imprinted polymers of a specific taste-producing molecule.

20 Claims, 2 Drawing Sheets

OTHER PUBLICATIONS

Winquist et al., "Handbook of Machine Olfaction—Electronic Tongues and Combinations of Artificial Senses", vol. 11 Issue 1, pp. 279-306, Published Online: Feb. 25, 2003.

International Business Machines Corporation, "Cantilever Based Gas Chromatography", Research Disclosure Database No. 453102, © Kenneth Mason Publications Ltd., 3 pages, Jan. 2002.

* cited by examiner

ELECTRONIC TONGUE SENSOR

RELATED APPLICATION

This patent application claims priority to U.S. provisional patent application Ser. No. 60/971,258, filed on Sep. 10, 2007, assigned to the assignee of the currently claimed subject matter.

BACKGROUND

1. Field

Subject matter disclosed herein relates to the field of electronic tongue sensors or the like.

2. Background Information

Sensing taste by human panel is employed in food and beverages industries to achieve taste consistence in food and beverage products. However, human taste panels sometimes give rise to more than 50% variation. Therefore, development of an 'objective' tool to sense taste is desirable. A common type of sensor used may employ electrochemical techniques, such as potentiometry and voltammetry. However, these detect electrochemically active compounds and, therefore, may not take into account other salient aspects of taste.

BRIEF DESCRIPTION OF DRAWING

Subject matter is particularly pointed out and distinctly claimed in the concluding portion of the specification. Claimed subject matter, however, both as to organization and method of operation, together with objects, features, and advantages thereof, may best be understood by reference of the following detailed description if read with the accompanying drawing in which:

DETAILED DESCRIPTION

Figure 1:
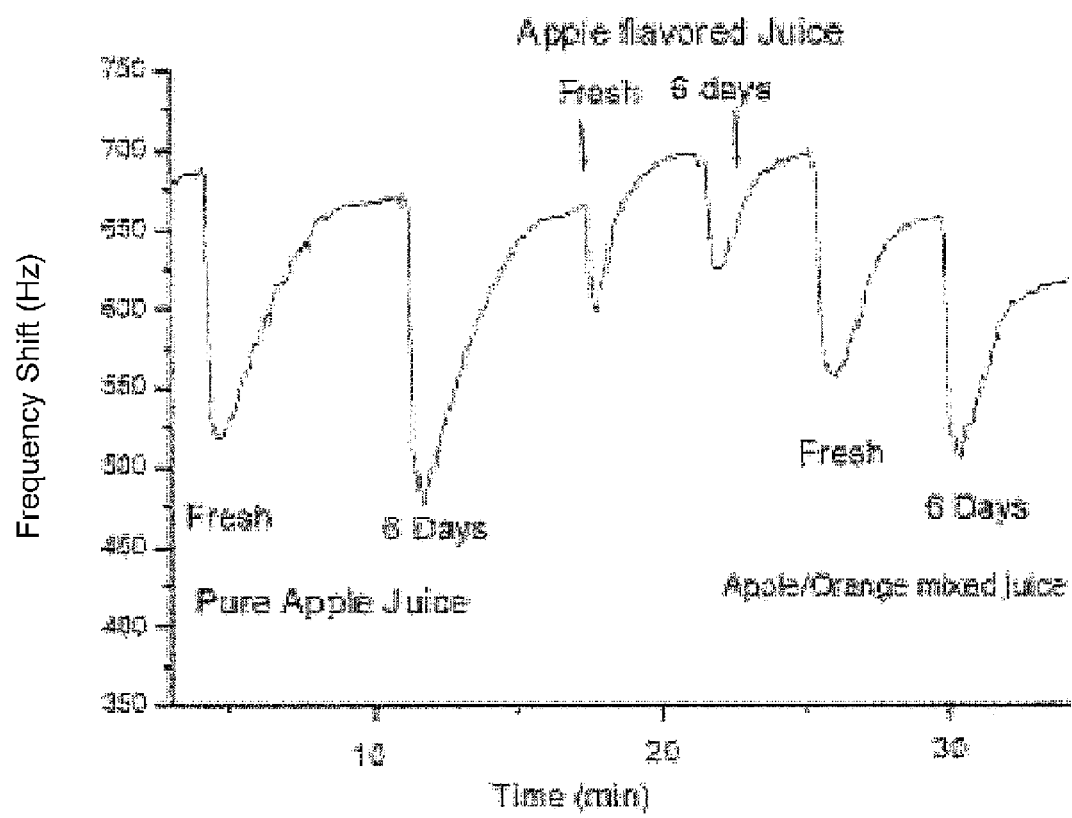
FIG. 1 is a plot showing results in terms of frequency shifts for various apple juices for an embodiment of an electronic tongue sensor.
Figure 2:
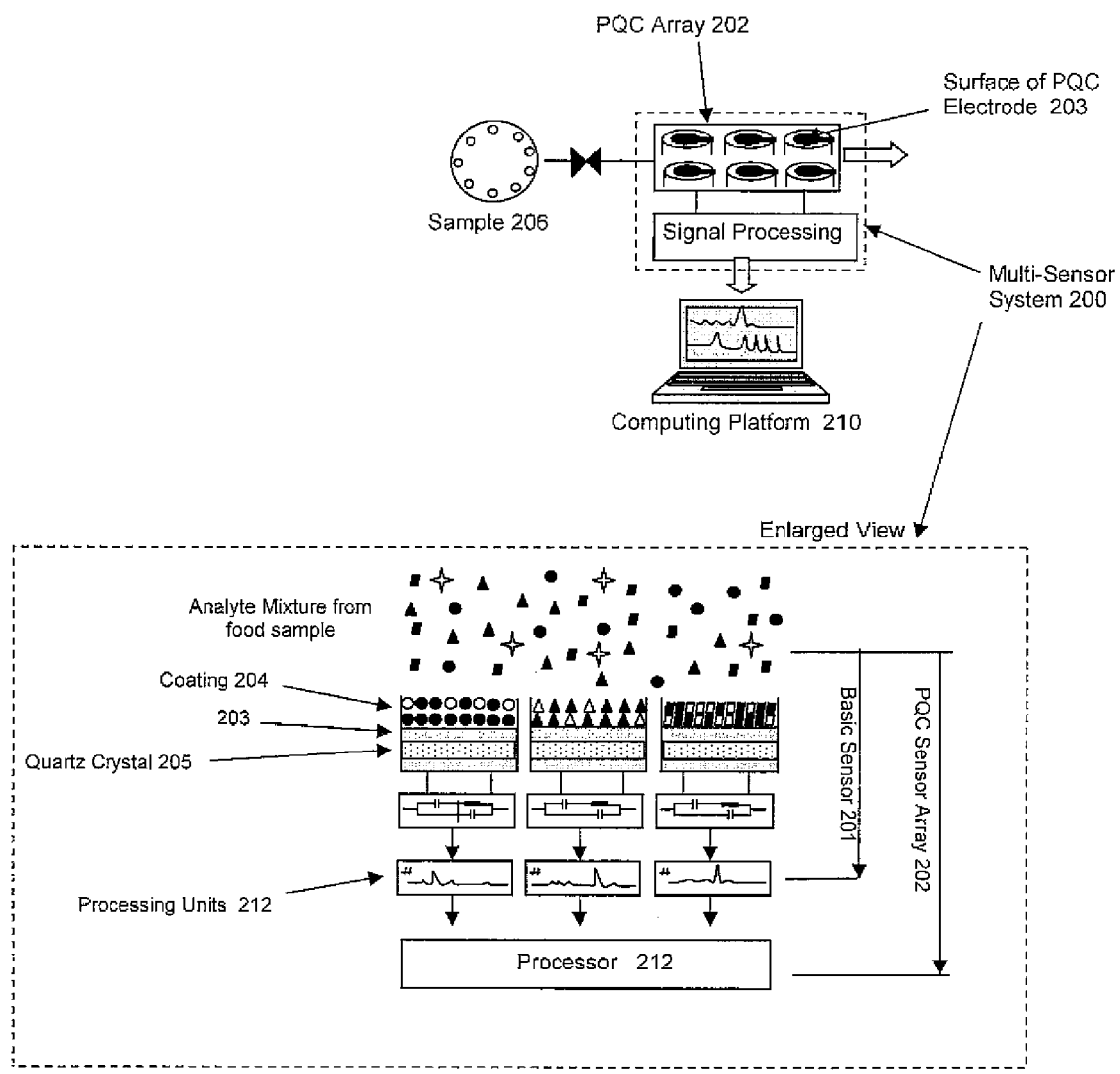
FIG. 2 is a schematic diagram depicting an embodiment of an electronic tongue system for sensing.

In the following detailed description, numerous specific details are set forth to provide a thorough understanding of claimed subject matter. However, it will be understood by those skilled in the art that claimed subject matter may be practiced without these specific details. In other instances, methods, apparatuses or systems that would be known by one of ordinary skill have not been described in detail so as not to obscure claimed subject matter.

Reference throughout this specification to "one embodiment" or "an embodiment" may mean that a particular feature, structure, or characteristic described in connection with a particular embodiment may be included in at least one embodiment of claimed subject matter. Thus, appearances of the phrase "in one embodiment" or "an embodiment" in various places throughout this specification are not necessarily intended to refer to the same embodiment or to any one particular embodiment described. Furthermore, it is to be understood that particular features, structures, or characteristics described may be combined in various ways in one or more embodiments. In general, of course, these and other issues may vary with the particular context of usage. Therefore, the particular context of the description or the usage of these terms may provide helpful guidance regarding inferences to be drawn for that context.

Likewise, the terms, "and," "and/or," and "or" as used herein may include a variety of meanings that also is expected to depend at least in part upon the context in which such terms are used. Typically, "or" as well as "and/or" if used to associate a list, such as A, B or C, is intended to mean A, B, and C, here used in the inclusive sense, as well as A, B or C, here used in the exclusive sense. In addition, the term "one or more" as used herein may be used to describe any feature, structure, or characteristic in the singular or may be used to describe some combination of features, structures or characteristics. Though, it should be noted that this is merely an illustrative example and claimed subject matter is not limited to this example.

Some portions of the detailed description which follow are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

As mentioned previously, sensing taste by human panel is employed in the food and beverages industries to achieve taste consistence in their products. However, electronic tongues were developed for improved quality control and quality assurance in taste consistence of food products. A number of possible embodiments of an electronic tongue are discussed in connection with the subject matter of the present application and claimed subject matter is not intended to be limited in scope to a particular embodiment. Nonetheless, as explained in more detail below, one example embodiment may include molecularly imprinting polymer coatings for piezoelectric quartz crystal multi-sensor systems 200. Such an approach may, for example, provide an electronic tongue with advantages over currently known approaches.

Traditional or state of the art technology for taste sensing in electronic tongue employs the use of an array of electrodes for potentiometric measurement by monitoring voltages or voltammetric measurement by monitoring currents. For example, Volf et al. described the cell setup for voltage monitor in 2002 (see CZ 294443) and a multisensor information system has been given by Ahlers in 2004 for voltage signals (see DE 10315848). A voltammetric measurement setup had been described in 2002 by Winquist et al. and Ekberg (see WO 2002-052254 and EP 1219957). A gas chromatography procedure with separation of analytes was given by International Business Machine Corporation in 2002 for electronic nose with extended coverage to electronic tongue using liquid chromatography. For application of electronic tongue, description has been given by Winquist et al. in 2002 for detecting ozone (see WO 2002-052254), Jansson et al. in 2003 for detecting urea in liquid (see WO 2003046554), Isz et al. in 2004 for assessing bitterness of active drugs (see US 2004-191918), and Winquist et al. in 1999 for assessing drugs in blood by detecting given markers (see WO 9913325). For taste assessment, Li et al in 2005 had disclosed genes of domestic dog for taste receptor which could be used to screen taste compounds for dogs and related uses (see WO 2005-12765). Chemometric approach based on pattern recognition with training phase had been described by Isz in 2004 using partial least square calculation for the bitterness of active drugs (see US 2004-191918). The multi-electrode arrays as described are developed with low specificity of given taste-causing molecules. It depends on chemometric calculation of the potentiometric signals and computer pattern recognition to identify a given taste against a standard taste, with typical successful matching of tastes in about 70% of the cases.

As suggested previously, variability between taste panels can sometimes give rise to more than 50% variation in terms of flavor units. Common types of sensors used are based on electrochemical techniques, such as potentiometry and voltammetry. However, such approaches detect electrochemically active compounds.

In recent years, there has been a growing interest in coated piezoelectric crystals, not only as highly sensitive and selective detector of various air pollutants but also as simple, inexpensive and portable devices. High sensitivity and simple relationship between mass and frequency make a quartz crystal a useful tool. It may be employed to study adsorption and as a selective chemical sensor in various applications.

The principle of the detection is that the frequency of vibration of an oscillating crystal is decreased by the adsorption of a foreign material on its surface. A gaseous pollutant is selectively adsorbed by a coating on the crystal surface, thereby increasing the weight of the crystal and decreasing the frequency of vibration. The decrease in the frequency is proportional to the increase in weight due to the presence of gas adsorbed on the coating according to the following equation: $\Delta F = K \times (\Delta C)$. Here, $\Delta F$ is the frequency change (Hz), K is a constant which refers to the basic frequency of the quartz plate, area coated, and a factor to convert the weight of injected gas (g) into concentration (ppm), and $\Delta C$ is concentration (ppm) of sample gas.

U.S. Pat. No. 3,164,004 teaches that a piezoelectric quartz crystal coated with a substrate selectively sensitive to changes in the atmospheric environment can serve as a detection device in fluid analyzers. In general, this discovery is based on the principle that the oscillation of a crystal, both in frequency and amplitude, is in part a function of its weight. The change in weight of a crystal coated with a substrate selectively sensitive to a particular contaminant if placed in an environment containing that contaminant is, in turn, at least partly a function of the concentration of the contaminant. Therefore, the measurement of change in oscillation characteristics of a coated crystal sensitive to a particular contaminant upon exposure to a given atmosphere is a direct and highly sensitive measure of the presence and concentration of that contaminant.

Variations of and improvements in this basic method are shown, inter alia, in the following publications U.S. Pat. Nos. 5,177,994; 5,817,921, and 6,085,576; Japanese Patents Nos. 1244335, and 5187986; European Patent No. 992768, and "Electronic Nose and Artificial neural Networks", L. Moy and M. Collins, American Chemical Society, Anal. Chem., 1986, 58, pp. 3077-3084; "Piezoelectric Crystal Sensor for the Determination of Formaldehyde in Air", Talanta, Vol. 38, No. 5, pp. 541-545, 1991; "Odor Sensing System Using Neural Network Pattern Recognition", Toyosaka Moriiznmi and Takamichi Nakamoto, International Conference on Industrial Electronics, Control, Instrumentation and Automation, Nov. 9-13, 1992, Marriot Mission Valley, San Diego, USA.

As described in more detail below, a piezoelectric quartz crystal element may be manufactured with a coating applied to be employed as an electronic tongue sensor. The use of a Piezoelectric Quartz Crystal (PQC) sensor based at least on interaction of taste-producing molecules with selective coatings at the PQC surface may provide a way to better mimic taste sensation. Its operation may resemble adsorptive interaction that takes place in the human tongue tasting process.

Research on developing quartz piezoelectric crystal (PQC) as chemical sensors for analysing organic vapors of health significance in workplace has taken place, as alluded to previously. The interaction of coating material with a vapor of interest may be examined via the measurement of frequency shift of the quartz crystal. The frequency of oscillation may decrease if the sensing material encounters specific gases or vapours, for example. Thus, quartz coated with one kind of sensing material could serve as a specific sensor for a particular gas or vapor. Subsequently, chemical sensors sensitive to ppm level of concentration have therefore been developed. Likewise, coating technology has been developed based at least in part on a self-assembled monolayer method capable of dense-packing of antibodies on quartz crystals and on computer technology for identification and apportionment of air pollution sources based on chemometric pattern recognition using Factor Analysis. These technologies therefore may enable the advancement of the quartz piezoelectric crystal detection as a technology platform to develop biosensors targetted on a selected serogroup of Salmonella, as well as to develop quartz chemical sensors based at least in part on volatile organic compounds (VOC) as an electronic nose to detect odous, identify sources, monitor industrial processes or assess quality of manufactured products emitting volatile organic vapors via an array of quartz detectors. Likewise, these approaches may enable advancement of electronic tongue technology using Molecularly Imprinted Polymer (MIP) Technology in conjunction with quartz technology for taste assessment in liquid food products, for example, as explained in more detail below. Of course, these intended as example embodiments and claimed subject matter is not intended to be limited in scope to the particular embodiments described.

Molecularly Imprinted Polymer (MIP) Technology may provide a possibility for recognition of taste-producing molecules. For example, in one possible approach, without limitation, re-arrangement of monomers with desirable chemical function groups during polymerisation may be employed to mimic the function of a taste bud(s) for taste-producing molecules. Such a process, for example, resembles imprinting molecular structure at MIP surface during polymerization that can be used to copy different types of molecules concurrently for taste recognition. Such a process may, for example, generate molecular clusters with a desirable stereo arrangement of functional groups at MIP which could coat onto a quartz sensor surface to provide recognition sites for taste-producing molecules. Signals obtained from PQC with MIP coatings may, for example, be processed by chemomertic techniques to provide an objective approach to identify a given taste and to quanity the degree of taste in liquid media for taste assessment in manufactured food products, as simply one example.

A fast or sensitive method to measure taste-producing compounds in drink, beverage or other food products is desirable. In one embodiment in accordance with claimed subject matter, a piezoelectric quartz crystal (PQC) sensor array 202 based at least in part on a molecularly imprinted polymer (MIP) coating 204 may sense molecules, such as quinine or saccharine, in bitter drinks or identify pure fruit juice from fruit flavored drink, as described in more detail below. A MIP-PQC sensor array was applied for sensing commercially available tonic water and fruit juice with results compared to taste assessment from a human taste panel. In addition to reducing cost and providing results in 24 hours, an MIP-PQC sensor array embodiment such as the one employed provided relatively fast sample throughput of 17-19 analysis per hour, satisfactory repeatability, and a high sensitivity to detecting change in bitter taste in tonic water and freshness of fruit juice as compared to a human taste panel. Thus, other embodiments may be employed to provide a methodology for taste application in flavor estimation, quality control of experimental, intermediate and final product for drinks, beverages and food industries, as well as other applications. Additionally, in an embodiment, a piezoelectric quartz crystal sensor 201 may comprise one or more quartz crystals 205 coated with metal electrodes 203 on both sides with diameters varying from about 5 to about 50 mm. Further, in an embodiment, a piezoelectric quartz crystal sensor 201 may comprise quartz crystals 205 coated with metal electrodes 203 on both sides capable of resonating at a frequency varying from about 1 to about 100 MHz.

In one or more embodiments in accordance with claimed subject matter, formation of a molecularly imprinted coating is undertaken. Two possible methods, for example, include precipitation or sol-gel surface imprinting. For example, a precipitation polymerization method may be used for imprinting bitter taste with quinine as a template or a sol-gel surface imprinting method may be used for imprinting fruit juice, although, again, claimed subject matter is not limited in scope to these two approaches. Of course, claimed subject matter is also not limited in scope to the particular details of these embodiments. These approaches may be employed in some embodiments without necessarily employing the details described below for these particular embodiments.

In one embodiment, for example, for precipitation of molecularly imprinting polymers to prepare nano-emulsion for production of specific polymer coatings for a piezoelectric quartz crystal 205 sensor, the following processes were followed:
(a) A template molecule such as quinine and saccharine and a monomer such as methacrylic acid (MAA) were added to a 50 ml round-bottom flask for dissolution in acetonitrile prior to precipitation polymerization. After 5 minutes, a cross-linker such as ethylene glycol dimethacrylate (EGDMA) and an initiator such as 2,2-Azobisisobutyronitrile (AIBN) were added. The mixture was purged with nitrogen for 5 minutes and the flask was sealed under this atmosphere. After 24 hours of precipitation polymerization in a thermostated water bath at 60° C., MIP particles were collected by centrifuge.
(b) Particles precipitated were washed extensively using a methanol/acetic acid solution (9:1, v/v) until the template molecule was no longer detected in the extraction solvent. The particles were then washed several times with methanol until the pH of the extracted solvent was neutral. The solvent was removed by centrifugation and the particles were dried under vacuum.

In another embodiment, for imprinting a fruit juice mixture, instead, a surface imprinting method was performed as follows:
(a) The surface of a PQC electrode 203 was modified with a thiol group by immersing it in 16 mM mercaptoethanol for 12 hours.
(b) Target juice was dried by a gentle blow of nitrogen, following by re-dissolution in 4 mL absolute ethanol under ultrasonication.
(c) 400 uL Ti(O-$^n$Bu)$_4$ was added to the above solution and it was shook for 4 hours.
(d) The mercaptoethanol-modified PQC electrode was immersed in the resulting solution for 20 minutes, and rinsed with absolute ethanol for 1 minute to remove physically adsorbed species and dried in nitrogen.
(e) The electrode was attached to a frequency counter and kept in ambient air until a shift in frequency, possibly occurring from the process of the hydrolysis of a surface alkoxide group, became relatively small.
(f) The forgoing procedure, (a) to (e), which constitutes one cycle of chemisorption and activation, gives rise to an imprinted TiO$_2$ gel film to mimic the target juice.

Several such cycles were conducted until the frequency of the PQC electrode was decreased by about 3000 Hz.
(g) To remove the bound template molecule, the film was immersed in ammonia solution (1% v/v) for 10 minutes, rinsed with deionized water and ethanol thoroughly, and dried with nitrogen.

As the discussion above illustrates, for this particular embodiment, for a coating of a PQC sensor with an imprinted Ti(O-$^n$Bu)$_4$ network produced by a sol-gel method, such a coating is formed during the imprinting process. However, for an embodiment employing a precipitation method, after formation of a coating, a PQC sensor may be fabricated.

For this latter particular embodiment, coating of a sensor 201 with polymer particles produced by a precipitation method was carried out using the following procedure:
(a) 1.6 mg of fine polymer powders was dispersed into 1 ml Tetrahydrofuran (THF) containing 0.5 mg of polyvinyl chloride (PVC) powders.
(b) Six micro liters of the suspension formed was spread onto the Au-electrode surface of the PQC.
(c) After Tetrahydrofuran (THF) was evaporated at room temperature in air, a polymer coating was formed on the electrode surface. The frequency shift was controlled to about $3.0 \times 10^3$ Hz.

Although claimed subject matter is not limited in scope to this particular example embodiment, to achieve functioning of an electronic tongue, 4 to 8 piezoelectric quartz crystal sensors with different specific coating were used under a continuous flow system. The following conditions may also be employed, although, again, these are merely illustrative examples.
(a) Flow rates may vary from 0.5 to 2 mL/min;
(b) Measuring cells may be arranged in a combination of serial or parallel format for measurement; and
(c) Frequency shift of PQC crystals may be measured by an interface board with a data sampling rate of 1 s, capable of measuring channels in parallel or in sequence and capable of transferring data to a computing platform for chemometric calculation or display of frequency shifts over a period of measurement.

Depending at least in part upon the conditions, a Quinine-MIP modified PQC sensor has displayed a linear working range for quinine from 10-1080 mg/L which follows a regression equation of $-\Delta F=1.54+0.25$ C (r=0.99). For the saccharine-MIP modified PQC sensor, it has displayed a linear working range for saccharine from 51-3420 mg/L which follows a regression equation of $-\Delta F=-1.57+0.062$ C (r=0.99). The limit of detection calculated according to 3 times the signal to noise standard deviation ratio (n=5) is 2.04 mg/L for quinine and 32.8 mg/L for saccharine. These detection limits are comparable to values found in the literature for human taste threshold values for quinine hydrochloride (32.4 mg/L) and saccharine (4.10 mg/L) respectively. Furthermore, a highly repeatable method to detect a minute change in taste at working concentrations is also desirable. Therefore, as discussed below, the performance of the human and electronic tongue were compared with results discussed in the following paragraphs.

A desirable feature of a sensor may also relate to performance against other substances often found in food. Thus, common additives and agents used in drinks and beverages were tested for their potential interference with an embodiment of an MIP-PQC sensor, such as those previously discussed, although claimed subject matter is not limited in scope to these embodiments, of course. For additives used at higher concentrations such as sucrose, citric acid, sodium bicarbonate and sodium benzoate, concentrations at 10 mmol/L were used for testing whereas those normally used at lower concentrations such as caffeine and vanillin, concentrations at 2.5 mmol/L were used to study their interfering effect. The frequency shifts resulting from these interferents are listed in Table 1 below. Results show that there is not significant interference for those commonly included substances in beverages except sucrose. Thus, diet tonic water was selected to provide the values in Table 1.

TABLE 1

| Interferents | Analyte* (mmol/L) | Frequency shift (Hz) | | |
|---|---|---|---|---|
| | | Quinine-MIP | Saccharine-MIP | Non-imprinted polymer |
| Quinine | 0.25 | 24 | 1 | 0 |
| Sodium Saccharine | 0.83 | 0 | 10 | −1 |
| Vanillin | 2.5 | 0 | 0 | 2 |
| Caffeine | 2.5 | 0 | 0 | −1 |
| Citric acid | 10 | 5 | 2 | 3 |
| Sodium benzoate | 10 | 4 | 3 | 4 |
| Sodium bicarbonate | 10 | −3 | 1 | 1 |
| Sucrose | 10 | 62 | 27 | 36 |

*1) The same concentrations are used for testing either quinine or saccharine;
2) The concentration of interferents listed are those commonly found in tonic water;
3) For quinine determination, the concentration of quinine and saccharine are 0.25 mmol/L and 0.83 mmol/L respectively. For saccharine determination, the concentration of quinine and saccharine are 0.25 mmol/L and 0.83 mmol/L respectively.

Another desirable aspect of a sensor may relate to comparing juice at different stage of storage and development. Samples for 100% original apple juice, apple flavored synthetic drink and apple/orange mixed juice was therefore flowed through an apple juice imprinted PQC sensor at a flow rate of 1 ml/mins. The relative change in frequency shift of the PQC sensor using the above samples 206 followed this decreasing sequence: 100% original apple juice (180 Hz)>apple/orange mixed juice (105 Hz)>apple flavored synthetic drink (60 Hz). Likewise, for 100% apple juice stored at room temperature for a week, a frequency shift was found to increase by 10% compared to that of fresh juice.

Thus, embodiments of an MIP-coated PQC sensor array may be employed to provide a sensitive and fast method for determining taste-producing compounds in tonic water at practical concentration ranges with fast sample throughput, such as, in this example, 17-19 analysis per hour. In addition, satisfactory repeatability (RSD <5%, n=3), absence of significant interference from some substances commonly found in drinks except sucrose and relatively high sensitivity to detect changes in bitter taste in tonic water with a less suppressing effect in the presence of saccharine as compared to a human taste panel; however, claimed subject matter is not limited in scope to these aspects. These results are merely provided for purposes of illustration.

Below are examples of possible embodiments, although claimed subject matter is not limited in scope to these examples.

EXAMPLE 1

To compare sensitivity of an embodiment of a MIP-PQC sensor and a human tongue to differentiate changes in bitter taste of tonic water, tonic water was diluted by distilled water to various concentrations and samples produced were subjected to sensing by a MIP-PQC sensor embodiment, such as described above, and at the same time by a human taste panel. Results are shown in Table 2 below. A high variability of a human taste panel is shown, particular at high quinine levels. Taste difference is detected at 20% dilution by distilled water for high quinine level as compared to 10% dilution at low quinine level. However, with an embodiment of a MIP-PQC sensor for detection, repeatability (RSD, n=3) at 70 mg/L and 35 mg/L quinine are 1.3% and 2.3% respectively. Thus, to detect change in bitter taste by a MIP-PQC sensor embodiment, the worst case within a 99% confidence level (for 2.33 standard deviation range) is dilution of the tonic water by distilled water to 1.8% and 3.2% for high and low quinine, respectively. The results, therefore, indicate that a sensor provides a more sensitive differentiator than a human taste panel to detect a change in bitter taste in tonic water at both high and low quinine concentrations.

TABLE 2

| Percentage of distilled water added to tonic water with specified quinine concentration | Response from individual panelist | | | | |
|---|---|---|---|---|---|
| | 1 | 2 | 3 | 4 | Panel consensus |
| A) 70 mg/L Quinine | | | | | |
| 5% | − | − | − | − | − |
| 10% | + | + | − | − | − |
| 15% | + | − | − | + | − |
| 20% | + | + | + | + | + |
| 30% | + | + | + | + | + |
| B) 35 mg/L Quinine | | | | | |
| 5% | + | − | + | − | − |
| 10% | + | + | + | + | + |
| 15% | + | + | + | + | + |
| 20% | + | + | + | + | + |
| 30% | + | + | + | + | + |

Note:
"+" means that the panelists perceive correctly the change in intensity of the bitterness of tonic water after specified dilution;
"−" means that the panelist cannot detect the change or perceive incorrectly the change in intensity of the bitterness of tonic water after specified dilution.

EXAMPLE 2

To evaluate the effect of saccharine on bitter taste of tonic water, saccharine was added to tonic waters containing low and high levels of quinine. The results are shown in Table 3 below. Here, this example indicates that presence of additional saccharine leads to a reduction in sensitivity in detecting differences in bitter taste by a human taste panel as shown by an increase from 20 to 30% dilution for high-quinine tonic water and from 10 to 20% dilution for low-quinine tonic water as compared to solutions with no saccharine added (e.g., as discussed above). Level of saccharine appears to exert a noticeable effect on reduction of sensitivity for detecting change in bitter taste, as it takes up to 30% dilution to detect change in bitter taste at high saccharine as compared to 20% for low saccharine bitter drink. Thus, addition of saccharine is shown to have a beneficial effect in reduction of bitter taste.

For taste detection of quinine in saccharine spiked tonic water, repeatability (RSD, n=3) at 70 mg/L and 35 mg/L quinine are 1.6% and 3.9% respectively, which are comparable with results with no additional saccharine. Therefore, repeatability seems to be independent of saccharine level in tonic water. Thus, to detect change in bitter taste in the presence of saccharine by an embodiment of an MIP-PQC sensor, the worst case within 99% confidence level (for 2.33 standard deviation range) is dilution of tonic water by distilled water to 2.2% and 5.3% for high and low quinine respectively. Compared with tonic water at low saccharine level, there are slight increases in percentage dilution for tonic water at high saccharine levels. However, the difference is small and the presence of saccharine in tonic water is shown to give a much less suppressing effect on a MIP-PQC sensor embodiment as compared to a human taste panel to detect a change in bitter taste.

TABLE 3

| Percentage of distilled water added to tonic water with specified quinine and saccharine level | Response from individual panelist | | | | |
|---|---|---|---|---|---|
| | 1 | 2 | 3 | 4 | Panel consensus |
| A) 170 mg/L Saccharine + 70 mg/L Quinine | | | | | |
| 5% | − | − | − | − | − |
| 10% | − | + | − | − | − |
| 15% | + | − | + | + | − |
| 20% | + | − | − | + | − |
| 30% | + | + | + | + | + |
| B) 85 mg/L Saccharine + 35 mg/L Quinine | | | | | |
| 5% | + | − | − | − | − |
| 10% | + | − | + | − | − |
| 15% | + | − | + | − | − |
| 20% | + | + | + | + | + |
| 30% | + | + | + | + | + |

Note:
"+" means that the panelists can perceive correctly the change in intensity of the bitterness of tonic water after specified dilution;
"−" means that the panelist can not detect the change or perceive incorrectly the change in intensity of the bitterness of tonic water after specified dilution.

EXAMPLE 3

Samples for 100% original apple juice, apple flavored synthetic drink and apple/orange mixed juice were passing through an embodiment of an apple juice imprinted PQC sensor at a flow rate of 1 ml/mins. The relative change in frequency shift of the PQC sensor embodiment in the presence of the above samples follows this sequence: 100% original apple juice (180 Hz)>apple/orange mixed juice (105 Hz)>apple flavored synthetic drink (60 Hz). If 100% apple juice was stored at room temperature for a week, the frequency shift resulting was also found to increase by 10% as compared to that of fresh juice. The results are shown in FIG. 1.

It will, of course, also be understood that, although particular embodiments have just been described, claimed subject matter is not limited in scope to a particular embodiment or implementation. For example, one embodiment may be in hardware, such as implemented to operate on a device or combination of devices, for example, whereas another embodiment may be in software. Likewise, an embodiment may be implemented in firmware or as any combination of hardware, software, or firmware, for example. Likewise, although claimed subject matter is not limited in scope in this respect, one embodiment may comprise one or more articles, such as a storage medium or storage media. This storage media, such as, one or more CD-ROMs or disks, for example, may have stored thereon instructions, that if executed by a system, such as a computer system, computing platform 210, or other system, for example, may enable an embodiment in accordance with claimed subject matter to be executed, such as one of the embodiments previously described, for example. As one potential example, a computing platform may include: one or more processing units or processors 212; one or more input/output devices, such as a display, a keyboard, or a mouse; one or more memories, such as static random access memory, dynamic random access memory, flash memory or a hard drive, although, again, claimed subject matter is not limited in scope to this example.

While there has been illustrated and described what are presently considered to be example embodiments, it will be understood by those skilled in the art that various other modifications may be made or equivalents may be substituted, without departing from claimed subject matter. One skilled in the art will realize that an unlimited number of variations to the above description are possible, and that the examples and the accompanying figures are merely to illustrate one or more particular implementations. Additionally, many modifications may be made to adapt an embodiment to a particular situation; however, such a modified embodiment nonetheless remains within the scope of claimed subject matter. It is intended that claimed subject matter not be limited to the particular embodiments disclosed, but that such claimed subject matter includes all embodiments falling within the scope of any appended claims or any equivalents thereof.

The invention claimed is:

1. A device for taste assessment in liquid food products comprising:
    an array of piezoelectric quartz crystal sensors with substantially round cross-section comprising at least one molecularly imprinted coating specific for sensing one or more of taste-producing molecules comprising one or more of quinine, saccharine, and the elements of fruit juice, a resonant frequency of one or more of the array of piezoelectric quartz crystal sensors to shift in response to a change of mass at a sensor surface.

2. The device of claim 1, wherein said at least one coating comprises molecularly imprinted polymers of a specific taste-producing molecule.

3. The device of claim 2, wherein said at least one coating is formed at a metal electrode surface of one or more of said array of piezoelectric quartz crystal sensors.

4. The device of claim 3, wherein said metal electrode surface comprises gold or silver.

5. The device of claim 1, wherein piezoelectric quartz crystals of said array of piezoelectric quartz crystal sensors comprise quartz crystals coated with metal electrodes on both sides with diameters varying from about 5 to about 50 mm.

6. The device of claim 5, wherein said piezoelectric quartz crystal sensors coated with metal electrodes comprise gold or silver electrodes.

7. The device of claim 1, wherein the piezoelectric quartz crystals of said array of piezoelectric quartz crystal sensors comprise quartz crystals coated with metal electrodes on both sides capable of resonating at a frequency varying from about 1 to about 100 MHz.

8. The device of claim 7, wherein said piezoelectric quartz crystal sensors coated with metal electrodes comprise gold or silver electrodes.

9. The device of claim 2, wherein said molecularly imprinted polymers are formed by precipitation polymerization or sol-gel surface imprinting.

10. The device of claim 1, wherein said array of piezoelectric quartz crystal sensors comprises multiple coatings specific for sensing multiple specific taste-producing molecules.

11. A method comprising:
coating a piezoelectric quartz crystal sensor having a substantially round cross-section with a molecularly imprinted coating specific for sensing a specific taste-producing molecule comprising one or more of quinine, saccharine, and the elements of fruit juice, a resonant frequency of one or more of the array of piezoelectric quartz crystal sensors to shift in response to a change of mass at a sensor surface.

12. The method of claim 11, wherein said piezoelectric quartz crystal sensor is incorporated into an array of piezoelectric quartz crystal sensors.

13. The method of claim 11, wherein said coating comprises: molecularly imprinting polymers of a specific taste-producing molecule.

14. The method of claim 13, wherein said coating is applied to a metal electrode surface of said piezoelectric quartz crystal sensor.

15. The method of claim 14, wherein said metal comprises gold or silver.

16. The method of claim 12, wherein said molecularly imprinting polymers comprises sol-gel surface imprinting.

17. The method of claim 12, wherein said molecularly imprinting polymers comprises precipitation polymerization.

18. A method comprising:
producing a continuous flow for an array of piezoelectric quartz crystal sensors having substantially round cross-section and with sensor coatings specific for sensing different specific taste-producing molecule; and measuring frequency shifts of said piezoelectric quartz crystal sensors, wherein said sensor coatings are formed by precipitation polymerization method for imprinting bitter taste with quinine and sweet taste with saccharine, or a sol-gel surface imprinting method for imprinting fruit juice, a resonant frequency of one or more of the array of piezoelectric quartz crystal sensors to shift in response to a change of mass at a sensor surface.

19. The method of claim 18, wherein the flow rate of said continuous flow is in the range from about 0.5 to 2 mL/min.

20. The method of claim 18, wherein said array includes a number of sensors in the range from 4 to 8.

* * * * *